United States Patent [19]

Hansen et al.

[11] Patent Number: 4,739,103

[45] Date of Patent: Apr. 19, 1988

[54] PERFLUOROCYCLOALKANE CARBONYL FLUORIDES AND THEIR DERIVATIVES

[75] Inventors: John C. Hansen; Patricia M. Savu, both of St. Paul, Minn.

[73] Assignee: Minnesota Mining and Manufacturing Company, St. Paul, Minn.

[21] Appl. No.: 697,513

[22] Filed: Feb. 1, 1985

[51] Int. Cl.[4] .................. C07C 69/75; C07C 55/40
[52] U.S. Cl. .................. 560/125; 260/544 F; 568/819; 568/831
[58] Field of Search ............... 260/544 F; 568/819 C, 568/831; 558/428, 431; 560/125

[56] References Cited

U.S. PATENT DOCUMENTS

| | | | |
|---|---|---|---|
| 2,713,593 | 7/1955 | Brice et al. | 260/535 |
| 2,717,871 | 9/1955 | Scholberg et al. | 204/59 |
| 3,336,376 | 8/1967 | Nychka et al. | 260/544 F |
| 3,699,156 | 10/1972 | Hollsnd et al. | 560/220 |
| 4,094,911 | 6/1978 | Mitsch et al. | 260/615 A |

FOREIGN PATENT DOCUMENTS

| | | | |
|---|---|---|---|
| 669002 | 12/1965 | Belgium | 260/544 F |
| 1015798 | 1/1966 | United Kingdom . | |

OTHER PUBLICATIONS

Vander Meer, Robert K. *Chemical Abstracts* vol. 100 (1984) #2205c. Also *Chemical Abstracts Formula Index* vol. 100 (1984) p. 484F.

Journal of the Chemical Society, Perkin Transactions I, No. 7, 1980, pp. 1507–1511, G. S. Phull et al.: "Fluorinations With Complex Metal Fluorides, Part 5.[1] Fluorination of Nitriles Over Caesium Tetrafluorocobaltate (III)[2]".

C. E. Snyder, Jr., et al., AIAA Aircraft Systems Technology Conference, Aug. 1981.

Deposited Publ. 1972, Viniti, 5849–5873; Chem. Abs. 85, 171132d.

Murza, M. M., Chuchelova, V. G. Izv. Vyssh. Unchebn. Zaved. Khim Tecknol. 79,22(3), 267–270; Chem. Abs. 91, 38968p.)

*Primary Examiner*—Donald B. Moyer
*Assistant Examiner*—L. Hendriksen
*Attorney, Agent, or Firm*—D. M. Sell; J. A. Smith; C. Truesdale

[57] ABSTRACT

Di- and tri-substituted perfluorocycloalkane compounds which have a cyclohexane or decahydronaphthalene nucleus are provided. These perfluorocycloalkane compounds are carbonyl fluorides and derivatives thereof.

3 Claims, No Drawings

PERFLUOROCYCLOALKANE CARBONYL FLUORIDES AND THEIR DERIVATIVES

This invention relates to perfluorocycloalkane carbonyl fluorides, and derivatives thereof.

A limited number of perfluorocycloalkane dicarboxylic acids and their derivatives are known. The cyclic dicarbonyl fluoride, 1,4-perfluorocyclohexane dicarbonyl fluoride,

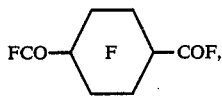

and certain derivatives, e.g. 1,4-perfluorocyclohexane dicarboxylic acid,

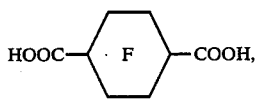

have been described (Murza, M.M., Chuchelova, V.G., Izv. Vyssh. Unchebn. Zaved. Khim Tecknol. 79, 22(3), 267-70; Chem. Abs. 91, 38968p). The ester derivative, dimethyl 1,4-perfluorocyclohexanedicarboxylate, has also been reported (Deposited Publ. 1972, VINITI, 5849-73; Chem. Abs. 85, 71132d).

The present invention provides novel di- or tri-substituted perfluorocycloalkane compounds which have a cyclohexane or decahydronaphthalene nucleus, said compounds being selected from the group consisting of
1,3-perfluorocyclohexane dicarbonyl fluoride,
1,3,5-perfluorocyclohexane tricarbonyl fluoride,
1,5-perfluoro(decahydronaphthalene) dicarbonyl fluoride,
2,6-perfluoro(decahydronaphthalene) dicarbonyl fluoride,
1,3-bis(hydroxymethyl)perfluorocyclohexane,
1,4-bis(hydroxymethyl)perfluorocyclohexane,
1,5-bis(hydroxymethyl)perfluoro(decahydronaphthalene),
2,6-bis(hydroxymethyl)perfluoro(decahydronaphthalene), and derivatives thereof.

Derivatives of the dicarbonyl fluorides include, for example, carboxylic acid, ester, amide, hydroxymethyl, nitrile, imide, triazine, and alkylcarbonyl derivatives and hexafluoropropylene oxide adducts. Derivatives of the (hydroxymethyl)perfluorocyclohexanes and the (hydroxymethyl)perfluoro(decahydronaphthalenes) include, for example, acrylate, urethane, glycidyl, allyloxy, bromomethyl, trifluoromethylsulfonate, cyanate, isocyanatomethyl, and aminomethyl derivatives.

Preferred perfluorocycloalkane compounds of the invention can be represented by the formulas

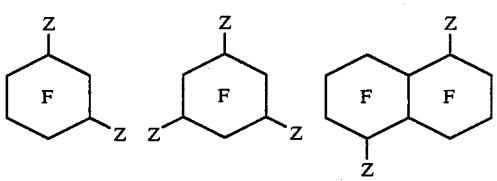

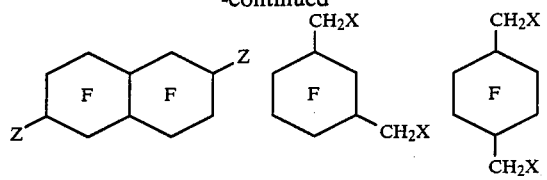

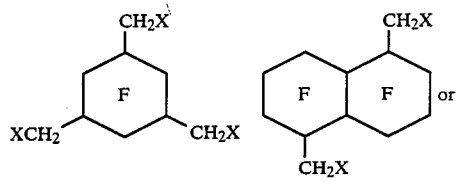

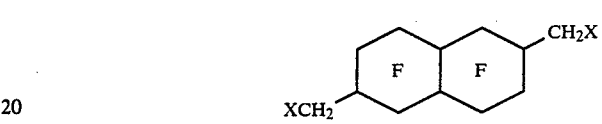

wherein each Z is independently a —COF group or a derivative thereof and each X is independently selected from the group consisting of OH, F, Cl, Br, $OCOCH=CH_2$, $OCOC(CH_3)=CH_2$, $OCH_2CH=CH_2$,

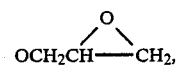

$NH_2$, NCO, $OSO_2CF_3$, and OCOR, where R is, for example, an alkyl, aryl, alkylaryl, or arylalkyl group having 1 to 12 carbon atoms and which R can contain up to six catenary oxygen atoms. (In the above-depicted structural formulas, the "F" within a ring structure conventionally denotes that the ring is perfluoro, i.e., all the ring carbon atoms are bonded to fluorine atoms and also may be bonded to Z or $CH_2X$.)

In a preferred subclass, Z is selected from the group consisting of COY, COOR, COOH, $COOM_{1/x'}$ $CF_2OCF(CF_3)COF$, $CF_2O[CF(CF_3)CF_2O]_yCF(CF_3)COF$, $CON(R')_2$, CN, and $C_3N_3(R_f)_2$, where Y is F, Cl or Br, M is an ammonium radical or a metal ion, for example, sodium or magnesium, x is the valence of M and preferably is 1, R is as described above, y is a number from about 1 to about 20, R' is H or said R, and $R_f$ is a perfluoroalkyl radical with 1 to 12 carbon atoms, which can contain up to four catenary oxygen atoms.

In accordance with another aspect of this invention, the perfluorocycloalkane carbonyl fluorides are made by electrochemical fluorination of the appropriate precursor cyclic hydrocarbon starting materials in liquid hydrogen fluoride following, for example, the procedures described in U.S. Pat. No. 2,717,871, which description is incorporated herein by reference. The crude acid fluoride products from such fluorination are then passed over sodium fluoride to remove residual hydrogen fluoride, filtered, and usually distilled to purify the product. The purified perfluorocycloalkane carbonyl fluorides thus obtained can be converted into various derivatives by conventional procedures, such as hydrolysis, esterification, reduction, and alkylation. Techniques for preparing a host of such derivatives are described, for example, in U.S. Pat. No. 4,094,911, which description is incorporated herein by reference.

Representative cyclic hydrocarbon precursors which can be fluorinated by electrochemical fluorination to yield acid fluoride compounds are precursors of the compounds of this invention include dimethyl isophthalate, dimethyl terephthalate, 1,5-dimethyl naphthalenedicarboxylate, 2,6-dimethyl naphthalenedicarboxylate, isophthaloyl chloride, and trimesoyl chloride.

Representative reaction schemes for preparing derivatives of the perfluorocycloalkane carbonyl fluorides include the following where R'$_f$ is a divalent or trivalent perfluorocycloalkane radical, e.g. having 6 to 12 carbon atoms, R is an alkyl, aryl, alkylaryl, or arylalkyl group, e.g. having 1 to 12 carbon atoms, and can contain up to six catenary oxygen atoms, and a and b are each independently a number from 0 to 20.

$$R'_f(COF)_2 + ROH \longrightarrow R'_f(COOR)_2$$

$$R'_f(COF)_2 + H_2O \longrightarrow R'_f(COOH)_2$$

$$R'_f(COF)_2 \xrightarrow{(H)} R'_f(CH_2OH)_2$$

$$R'_f(CH_2OH)_2 + CH_2=CR^3COCl \longrightarrow$$

$$R'_f(CH_2OCOCR^3=CH_2)_2$$

$$R'_f(COF)_2 + HN(R')_2 \longrightarrow R'_f[CON(R')_2]_2$$

$$R'_f(CH_2OH)_2 + CF_3SO_2F \longrightarrow R'_f(CH_2OSO_2CF_3)_2$$

$$R'_f(CH_2OSO_2CF_3)_2 + KBr \longrightarrow R'_f(CH_2Br)_2$$

$$R'_f(CH_2OSO_2CF_3)_2 + NH_3 \longrightarrow R'_f(CH_2NH_2)_2$$

$$R'_f(CH_2OH)_2 + CH_2\underset{\underset{O}{\diagdown\,\diagup}}{\text{—}}CHCH_2Cl \longrightarrow$$

$$R'_f(CH_2OCH_2\underset{\underset{O}{\diagdown\,\diagup}}{CH}CH_2)_2$$

$$R'_f(CH_2OH)_2 + R(NCO)_2 \longrightarrow$$

$$[RNHCOOCH_2R'_fCH_2OCONH]_n$$

$$R'_f(CH_2OH)_2 + RNCO \longrightarrow R'_f(CH_2OCONHR)_2$$

$$R'_f(COF)_2 + (a + b + 2)CF_3CF\underset{\underset{O}{\diagdown\,\diagup}}{\text{—}}CF_2 \xrightarrow{F^-}$$

$$\underset{\underset{CF_3}{|}}{FCOCF}(OCF_2\underset{\underset{CF_3}{|}}{CF})_aOCF_2R'_fCF_2O(\underset{\underset{CF_3}{|}}{CFCF_2}O)_b\underset{\underset{CF_3}{|}}{CFCOF}$$

The compounds of this invention are useful as monomers, chemical intermediates, crosslinking agents, and inert fluids. Lower alkyl esters of 1,3-perfluorocyclohexane dicarboxylate have a wide liquid range, good chemical stability and do not support combustion, and thus are useful for applications such as pump and hydraulic fluids, vapor phase heating fluids, and heat transfer fluids.

The product of the electrochemical fluorination process and the compositions prepared therefrom which make up a major amount of the composition, i.e., generally at least 50 weight percent and usually up to 70 weight percent, are generally a mixture of perfluorocycloalkane products. In addition, small amounts of by-products, such as ring-contracted, ring-opened, and ring-expanded compounds, can be present in the mixtures or reaction products as a result of the reaction conditions involved in their preparation. The presence of such by-products, in amounts up to 50 weight percent of the reaction product, but generally less than 30 weight percent of the reaction product, generally does not affect the usefulness of the perfluorocycloalkanes in admixture therewith.

The following nonlimiting examples illustrate the preparation of compounds of this invention, shown below in Table 1.

TABLE 1

| Compound No. | Example No. | Structure |
|---|---|---|
| 1 | 1 | 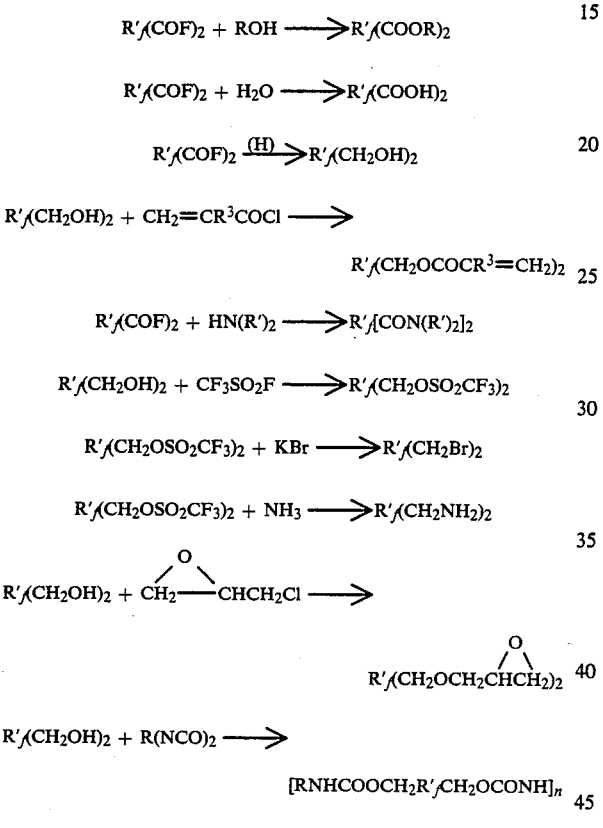 |
| 2 | 2 | 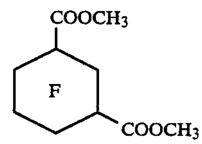 |
| 3 | 3 | 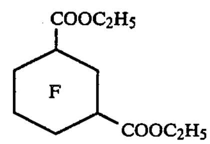 |
| 4 | 4 | 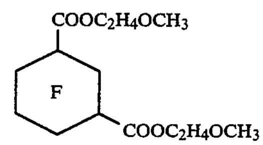 |
| 5 | 5 | 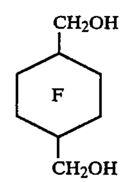 |
| 6 | 6 | 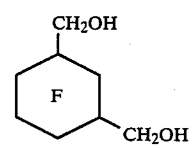 |
| 7 | 7 | 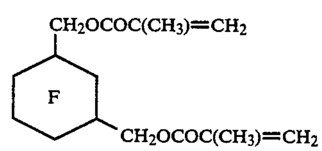 |
| 8 | 8 | 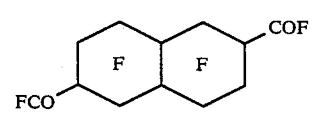 |

TABLE 1-continued

| Compound No. | Example No. | Structure |
|---|---|---|
| 9 | 9 | 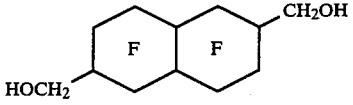 |
| 10 | 14 | 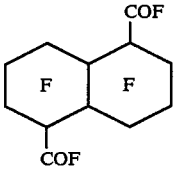 |
| 11 | 15 | 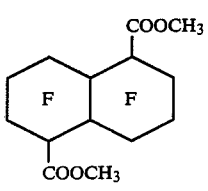 |
| 12 | 10 | 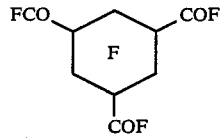 |
| 13 | 11 | 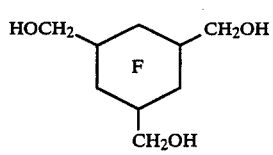 |
| 14 | 12 | 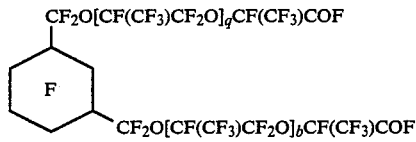 |
| 15 | 12 | 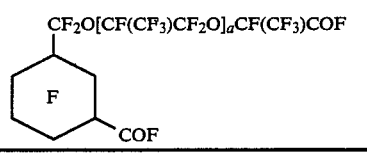 |

EXAMPLE 1

A 50 ampere cell of the type described in U.S. Pat. No. 2,713,593 was charged with 1500 g anhydrous liquid hydrogen fluoride. A solution of 3300 g dimethyl isophthalate and 350 g dimethyldisulfide in 1900 g anhydrous liquid hydrogen fluoride was charged periodically to the cell with additional hydrogen fluoride as make-up. The cell was operated continuously at 5.5 to 6.5 volts, 50 amps, 40° C., and 1.05 kg/cm². The gaseous product mixture from the cell was condensed and the liquid fluorocarbon product mixture, present as a lower layer, was separated from the hydrogen fluoride layer to yield 4470 g of crude fluorochemical products. The crude liquid fluorochemical products were treated with sodium fluoride, filtered and distilled to yield distillate having a boiling range of 95 to 115° C. and containing about 60 weight percent 1,3-perfluorocyclohexane dicarbonyl fluoride, compound 1 of Table 1, as determined by gas chromatography, fluorine and proton nuclear magnetic resonance, and infrared spectral analysis.

EXAMPLE 2

Slowly added to 110 ml of 12 weight percent $BF_3$ in methanol were 110 g of the distillate of Example 1, containing mainly 1,3-perfluorocyclohexane dicarbonyl fluoride, compound 1 of Table 1, having a boiling point of 95°-115° C. The mixture was stirred vigorously and reacted for 4 hours. To this reaction product were added 100 ml water and the fluorochemical phase which separated was dried with silica gel and distilled. After stripping the reaction mixture at water aspirator pressure, the fluorochemical phase was distilled to yield 54.2 g of material boiling at 87°-95° C. at 5 torr. Proton and fluorine nuclear magnetic resonance (nmr) spectra and the infrared spectrum of the distilled fluorochemical phase were consistent with dimethyl 1,3-perfluorocyclohexane dicarboxylate, compound 2 of Table 1. This compound had a boiling point of 210°-220° C. and a pour point of −42° C.

EXAMPLE 3

Following the procedure of Example 2, 114 g of the distillate of Example 1 were treated with 125 ml of absolute ethanol. After product isolation, 52.8 g of material distilling between 205°-230° C. at atmospheric pressure was obtained. Fluorine and proton nuclear magnetic resonance spectra and the infrared spectrum of the material were consistent with diethyl 1,3-perfluorocyclohexane dicarboxylate, compound 3 of Table 1.

The physical properties of the diethyl 1,3-perfluorocyclohexanedicarboxylate are set forth in Table 2 together, for comparative purposes, with physical properties of FC-70, a commercially available perfluorinated inert fluid produced by 3M Company.

TABLE 2

| Physical Properties of Compound 3 and FC-70 | | |
|---|---|---|
| | Fluid | |
| Property | Compound 3 | FC-70 |
| Bp, °C. | 210–230 | 215 |
| Pour pt. °C. | −70 | −25 |
| Vapor pressure, microns | | |
| at 40° C. | 26 | 320 |
| at 60° C. | 244 | 1300 |
| Viscosity (centipoise) at | | |
| −42° C. | 2527 | — |
| −18 | 70 | — |
| 4 | 14 | 90 |
| 22 | 6.5 | 19 |
| 70 | 2.4 | 2.1 |
| 90 | 1.7 | 1.3 |

As can be seen from the data in Table 2, although the compound 3 of the invention has a boiling point comparable to FC-70, compound 3 has a lower pour point, vapor pressure, and viscosity which are desirable physical properties for inert fluid applications.

The heat of combustion, a property related to flammability, of compound 3 is compared with various aircraft hydraulic fluids in Table 3.

TABLE 3

| Fluid | Heat of combustion (kcal/kg) |
| --- | --- |
| Compound 3 | 2,897 |
| Phosphate ester* | 7,200 |
| Synthetic hydrocarbon* | 10,000 |
| Poly(chlorotrifluoroethylene)* | 1,250 |

*C. E. Snyder, Jr., et al, AIAA Aircraft Systems Technology Conference, August 1981.

From the data in Table 3, it can be seen that compound 3 has a low heat of combustion, indicative of low flammability properties. To further illustrate the low flammability of Compound 3, about 50 g of the compound was placed in an open 50 ml beaker. A flame held at the surface of the fluid failed to ignite the fluid, further demonstrating the low flammability of compound 3.

Compounds 2 and 3 were tested for chemical stability by exposure to potassium hydroxide, sulfuric acid, ammonia, ammonia/methanol, and potassium permanganate under various test conditions. The reagents, conditions and amount of compound recovered are set forth in Table 4. For comparative purposes, the chemical stability of dimethyl 1,4-perfluorocyclohexanedicarboxylate was also determined.

TABLE 4

Chemical Stability of Esters 2 and 3

| Compound | Reagent | Conditions | Recovery, % |
| --- | --- | --- | --- |
| 2 | 20% KOH(aq) | 4 hr, 50° C. | 59 |
| 3 | 20% KOH(aq) | 6 hr, 100° C. | 40 |
| 3 | 50% H$_2$SO$_4$(aq) | 6 hr, 100° C. | 95 |
| 2 | 20% KMnO$_4$(aq) | 6 hr, 100° C. | 90 |
| 2 | — | 6 hr, 220° C. | 95 |
| 3 | NH$_3$[b] | 6 hr, 22° C. | 57 |
| 3 | NH$_3$[b], CH$_3$OH[c] | 6 hr, 22° C. | 71 |
| a | NH$_3$[b], CH$_3$OH[c] | 6 hr, 22° C. | 6 |
| a | 20% KOH(aq) | 4 hr, 50° C. | 61 |

[a]Dimethyl 1,4-perfluorocyclohexanedicarboxylate
[b]NH$_3$ bubbled continuously through compound
[c]Compound diluted 50% with methanol As shown, the chemical stability of compound 3 towards ammonia/methanol is greatly superior to that of dimethyl 1,4-perfluorocyclohexanedicarboxylate, illustrating the surprising chemical stability, especially to nucleophilic reagents, of the 1,3-perfluorocyclohexane dicarboxylate ester isomers compared with the 1,4-isomers of perfluorocyclohexanedicarboxylate esters.

EXAMPLE 4

Placed in a plastic bottle and cooled to 0° C. were 500 ml methoxy ethanol. Slowly added to the bottle with stirring over a one hour period were 208 g distillate prepared as Example 1. The reaction mixture was stirred at room temperature for an additional hour. Added to the reaction mixture were 1400 ml water and the fluorochemical layer was allowed to separate. This layer was then distilled at atmospheric pressure. A total of 117 g of material boiling in the range of 98°-162° C. was collected. The pot residue was distilled at a pressure of 2.5 torr to yield 9.9 g material boiling at 65°-130° C., and 161 g of product boiling at 130°-140° C. The latter reaction product was passed through a small column of silica gel, and the silica washed with 50 ml of diethyl ether. The ether solvent was removed from the total eluent on a rotary evaporator under reduced pressure to yield 157 g of product. Proton and fluorine nmr spectra and the infrared spectrum obtained on the product were consistent with compound 4 of Table 1, di(methoxyethyl) 1,3-perfluorocyclohexanedicarboxylate. The pour point of this ester was −43° C.

EXAMPLE 5

Slurried in 170 ml of dimethoxyethane were 27 g sodium borohydride. Added to the reaction flask with vigorous stirring over a period of one hour were 146 g distillate containing 1,4-perfluorocyclohexane dicarbonyl fluoride (55% diacyl content, boiling at 96° to 110° C.), prepared as in Example 1, substituting dimethyl terephthalate for the dimethyl isophthalate. The reaction mixture was heated at reflux and stirred for three hours. After the reaction mixture had cooled to room temperature, it was poured into 100 ml of 10% aqueous sulfuric acid. The fluorochemical layer was separated and the aqueous phase was extracted with 100 ml of chloroform. The chloroform extract and fluorochemical phase were combined, dried with magnesium sulfate, stripped at a rotary evaporator under reduced pressure, and the residual liquid distilled at 1.5 torr to yield the following fractions:

| Weight(g) | Boiling Range (°C.) |
| --- | --- |
| 7.3 | 30–36 |
| 22 | 36–48 |
| 17 | 48 |

The fraction boiling at 48° C. and the pot residue (53 g) were combined and analyzed. Proton and fluorine nmr spectra and the infrared spectrum were consistent with compound 5 of Table 1, 1,4-bis(hydroxymethyl)perfluorocyclohexane.

EXAMPLE 6

Slurried in 160 ml of dimethoxyethane were 17 g sodium borohydride. Added to the reaction flask with vigorous stirring over a period of one hour were 100 g distillate prepared as in Example 1 and containing 59% 1,3-perfluorocyclohexane dicarbonyl fluoride. The reaction was carried out as in Example 5. The residual liquid obtained after stripping at the rotary evaporator was distilled at a pressure of 1.5 torr to yield 18.8 g of product boiling in the range of 30°-50° C., and 50.6 g boiling at 50°-70° C. Proton and fluorine nmr spectra and infrared spectrum of the latter higher boiling fraction were consistent with compound 6 of Table 1, 1,3-bis(hydroxymethyl)perfluorocyclohexane.

EXAMPLE 7

Placed in a flask under a dry nitrogen atmosphere were 10.1 g of compound 6, obtained from Example 6, 5 ml triethylamine, and 50 ml of methylene chloride. The reaction mixture was cooled to 0° C. and 5.1 ml (5.44 g) of methacryloyl chloride was added over a 5 minute period. The reaction mixture was stirred at room temperature for 1.5 hours, filtered, and extracted with 25 ml of 5% aqueous hydrochloric acid. The aqueous layer was extracted with 25 ml of methylene chloride and the combined organic layers were extracted with saturated aqueous sodium bicarbonate solution and dried over anhydrous magnesium sulfate. Solvents were removed at water aspirator pressure and finally at a reduced pressure of about 1.5 torr for two hours to remove all volatiles. The product thus obtained as a residual liquid weighed 11.7 g. Proton and fluorine nmr spectra and infrared spectrum of the product were consistent with the dimethacrylate ester of 1,3-bis(hydroxymethyl)perfluorocyclohexane, compound 7 of Table 1. The purity of the product was about 90%. The methyl ether of hydroquinone, 200 ppm, was added to the product as a polymerization inhibitor.

EXAMPLE 8

A reaction was carried out following the procedure of Example 1, except that 2,6-dimethyl naphthalene dicarboxylate was substituted for the dimethyl isophthalate. The resulting crude fluorochemical products were treated with sodium fluoride and distilled to yield distillate having a boiling point of 155° to 175° C. containing 69 percent 2,6-perfluoro(decahydronaphthalene) dicarbonyl fluoride, compound 8 of Table 1.

EXAMPLE 9

Following the procedure of Example 5, except using bis(2-methoxyethyl) ether in place of dimethoxyethane, 40 g of the distillate containing 2,6-perfluoro(decahydronaphthalene) dicarbonyl fluoride, compound 8 of Table 1, prepared in Example 8, were reacted with 4.0 g of sodium borohydride. The isolated product obtained on stripping the reaction solvent at 100° C. and 1.5 torr, was identified by proton nmr and mass spectral analysis as mainly the desired 2,6-bis(hydroxymethyl)perfluoro(decahydronaphthalene) compound 9 of Table 1.

EXAMPLE 10

A reaction was carried out following the procedure of Example 1, except that trimesoyl chloride was substituted for the dimethyl isophthalate. The resulting crude fluorochemical products were treated with sodium fluoride and distilled to yield distillate having a boiling range between 110° and 128° C. and containing 52 weight percent 1,3,5-perfluorocyclohexane tricarbonyl fluoride, compound 13 of Table 1.

EXAMPLE 11

To 21.4 g of sodium borohydride slurried in 100 ml of dimethoxyethane, there was added over a period of one hour with vigorous stirring, 90 g of the distillate of Example 10, a mixture containing 52 weight percent 1,3,5-perfluorocyclohexane tricarbonyl fluoride, compound 12 of Table 1, 40 weight percent 1,3-perfluorocyclohexane dicarbonyl fluoride, compound 1 of Table 1, and 8 weight percent perfluorocyclohexane. The mixture was heated at reflux and stirred for five hours. The resulting mixture was phase separated, extracted, and distilled as in Example 5. The residual product obtained after removal of solvent was identified by proton and fluorine nmr spectroscopy, infrared analysis and mass spectral analysis as a mixture of 1,3-bis(hydroxymethyl)perfluorocyclohexane, compound 6, and 1,3,5-tris(hydroxymethyl)perfluorocyclohexane, compound 13 of Table 1.

EXAMPLE 12

To 40 ml of dry dimethoxyethane and 1.97 g of cesium fluoride were added 50 g distillate prepared as in Example 1 and containing mainly 1,3-perfluorocyclohexane dicarbonyl fluoride. The reaction mixture was stirred for one hour at room temperature and then cooled to −22° C. A total of 58 g of hexafluoropropylene oxide was added over a period of 3 hours. The reaction mixture was then allowed to warm to room temperature overnight with stirring. The fluorochemical layer was distilled. Fraction 1 weighed 34.0 g and consisted of unreacted monocarbonyl and dicarbonyl fluorides with a boiling range of 52°–104° C. Fraction 2 weighed 16.5 g and had a boiling range of 104°–150° C.; gas chromatography analysis revealed Fraction 2 to be 26% unreacted carbonyl fluorides, 57 weight percent 1:1 adducts, and 17 weight percent 2:1 adducts. Fraction 3 weighed 29.5 g with a boiling range of 150°–200° C.; gas chromatography revealed Fraction 3 to be 7 weight percent unreacted carbonyl fluorides, 29 weight percent 1:1 adducts, 50 weight percent 2:1 adducts and 13 weight percent 3:1 adducts. Fluorine nmr analysis of fraction 3 was consistent with the gas chromatography analysis and the hexafluoropropylene oxide adducts of 1,3-perfluorocyclohexane dicarbonyl fluoride, compounds 14 and 15 of Table 1.

EXAMPLE 13

Placed in a reaction flask and cooled to 0° C. were 250 ml water. Added to the reaction flask by addition funnel over a period of 1.5 hours were 300 g distillate containing 1,3-perfluorocyclohexane dicarbonyl fluoride, prepared as in Example 1. After the addition was complete, the fluorochemical phase was separated from the aqueous phase. The fluorochemical phase was stripped at 20 torr by aspirator until the head temperature reached 80° C. The residue weighed 232.0 g. Infrared analysis of the residue was consistent with 1,3-perfluorocyclohexane dicarboxylic acid.

EXAMPLE 14

A reaction was carried out following the procedure of Example 1, except that dimethyl 1,5-naphthalene dicarboxylate was substituted for the dimethyl isophthalate. The resulting crude fluorochemical products were treated with sodium fluoride and distilled to yield distillate having a boiling point between 168 and 185° C. and containing 16 percent 1,5-perfluoro(decahydronaphthalene) dicarbonyl fluoride, compound 10 of Table 1.

EXAMPLE 15

Treated with 0.97 g of a 15:1 methanol:$BF_3$ complex were 9.4 g of distillate of Example 14 containing 1,5-perfluoro(decahydronaphthalene) dicarbonyl fluoride. After agitating for two minutes, 2.6 g of water were added and the fluorochemical phase was separated. Gas chromatography and infrared analysis of the fluorochemical phase were consistent with dimethyl 1,5-perfluoro(decahydronaphthalene) dicarboxylate, compound 11 of Table 1.

Various modifications and alterations of this invention will be apparent to those skilled in the art without departing from the scope and spirit of this invention and this invention should not be restricted to that set forth herein for illustrative purposes.

What is claimed is:

1. A perfluorocycloalkane compound of the formula

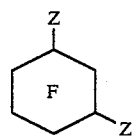

wherein Z is selected from —$COOCH_3$, —$COOC_2H_5$, and $COOC_2H_4OCH_3$.

2. A perfluorocycloalkane compound of the formula
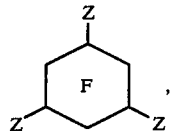
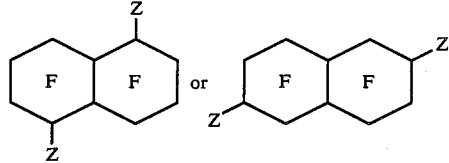
where Z is —COF.
3. A perfluorocycloalkane compound of the formula
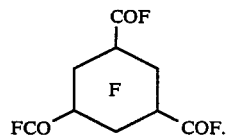
* * * * *